(12) United States Patent
Lee

(10) Patent No.: US 8,355,798 B2
(45) Date of Patent: Jan. 15, 2013

(54) SYSTEM AND METHOD FOR INCREASING RELATIVE INTENSITY BETWEEN CATHODES AND ANODES OF NEUROSTIMULATION SYSTEM USING PULSE SLICING

(75) Inventor: Dongchul Lee, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 508 days.

(21) Appl. No.: 12/612,528

(22) Filed: Nov. 4, 2009

(65) Prior Publication Data

US 2010/0121416 A1 May 13, 2010

Related U.S. Application Data

(60) Provisional application No. 61/113,442, filed on Nov. 11, 2008.

(51) Int. Cl.
*A61N 1/08* (2006.01)
(52) U.S. Cl. .................. 607/74; 607/72; 607/2
(58) Field of Classification Search .............. 607/69–74, 607/76
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,167,754 B1* | 1/2007 | Peeters et al. | 607/57 |
| 7,539,538 B2 | 5/2009 | Parramon et al. | |
| 7,650,184 B2 | 1/2010 | Walter | |
| 7,684,866 B2* | 3/2010 | Fowler et al. | 607/45 |
| 2003/0139781 A1 | 7/2003 | Bradley et al. | |
| 2005/0267546 A1 | 12/2005 | Parramon et al. | |
| 2007/0142863 A1 | 6/2007 | Bradley | |
| 2007/0150036 A1 | 6/2007 | Anderson | |
| 2007/0168004 A1 | 7/2007 | Walter | |
| 2007/0168007 A1 | 7/2007 | Kuzma et al. | |

(Continued)

FOREIGN PATENT DOCUMENTS

WO WO 2009/139968 A2 11/2009

OTHER PUBLICATIONS

PCT International Search Report for PCT/US2009/063286, Applicant: Boston Scientific Neuromodulation Corporation, Form PCT/ISA/210 and 220, dated Mar. 3, 2010 (8 pages).

(Continued)

*Primary Examiner* — Brian T Gedeon
(74) *Attorney, Agent, or Firm* — Vista IP Law Group LLP

(57) ABSTRACT

A method and neurostimulation system for providing therapy to a patient is provided. A plurality of electrodes is placed adjacent to tissue of the patient. A plurality of first electrical pulses is delivered to a first set of the electrodes, at least a second electrical pulse is delivered to a second set of the electrodes during the deliverance of each of the first electrical pulses, and at least a third electrical pulse is delivered to a third set of the electrodes during the deliverance of each of the first electrical pulses. The first electrical pulses have a first polarity, and each of the second electrical pulse(s) and third electrical pulses(s) has a second a second polarity opposite to the first polarity. The second and third electrical pulses are temporarily offset from each other.

25 Claims, 12 Drawing Sheets

U.S. PATENT DOCUMENTS

| | | |
|---|---|---|
| 2009/0024189 A1 | 1/2009 | Lee et al. |
| 2009/0131995 A1* | 5/2009 | Sloan et al. ........................ 607/3 |
| 2009/0132010 A1* | 5/2009 | Kronberg ......................... 607/72 |
| 2010/0121409 A1 | 5/2010 | Kothandaraman et al. |

OTHER PUBLICATIONS

PCT Written Opinion of the International Search Authority for PCT/US2009/063286, Applicant: Boston Scientific Neuromodulation Corporation, Form PCT/ISA/237, dated Mar. 3, 2010 (6 pages).

U.S. App. No. 60/951,177, Use of Stimulation Pulse Shape to Control Neural Recruitment Order and Clinical Effect, Inventor: Dongchul Lee, et al., filed Jul. 20, 2007.

PCT International Preliminary Report on Patentability (Chapter I of the Patent Cooperation Treaty) for PCT/US2009/063286, Applicant: Boston Scientific Neuromodulation Corporation, Form PCT/IB/326 and 373, dated May 26, 2011 (8pages).

* cited by examiner

SYSTEM AND METHOD FOR INCREASING RELATIVE INTENSITY BETWEEN CATHODES AND ANODES OF NEUROSTIMULATION SYSTEM USING PULSE SLICING

RELATED APPLICATION

The present application claims the benefit under 35 U.S.C. §119 to U.S. provisional patent application Ser. No. 61/113,442, filed Nov. 11, 2008. The foregoing application is hereby incorporated by reference into the present application in its entirety.

FIELD OF THE INVENTION

The present invention relates to tissue stimulation systems, and more particularly, to a system and method for conditioning and stimulating nerve fibers.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled to the stimulation lead(s). Thus, electrical pulses can be delivered from the neurostimulator to the stimulation lead(s) to stimulate or activate a volume of neural tissue. In particular, electrical energy delivered between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude and duration of the current pulses. The stimulation regimen will typically be one that provides stimulation energy to all of the target tissue that must be stimulated in order to provide the therapeutic benefit, yet minimizes the volume of non-target tissue that is stimulated. In the case of SCS, such a therapeutic benefit is "paresthesia," i.e., a tingling sensation that is effected by the electrical stimuli applied through the electrodes.

While the electrical stimulation of neurons has generally been successful in providing a therapeutic benefit to the patient, there are instances where the target tissue is not directly adjacent to an electrode and, because the electrical field strength decreases exponentially with distance from the electrodes, a relatively strong electrical field must be created to generate APs in the target neural fibers. The electrical field may, however, also result in the generation of APs in the non-target neural fibers between the electrode and the target neural fibers. The generation of APs in the non-target neural fibers may, in turn, lead to undesirable outcomes (e.g., discomfort or involuntary movements) for the patient. Because the target neural tissue (i.e., the tissue associated with the therapeutic effects) and non-target neural tissue (i.e., the tissue associated with undesirable side effects) are often juxtaposed, therapeutically stimulating neural tissue while preventing side effects may be difficult to achieve. In the context of SCS, there may be a few ways of eliminating, or at least minimizing, the stimulation of non-target neural tissue.

For example, in the case where the electrode array is medio-laterally aligned (i.e., the electrodes are arranged transversely to the neural fibers of the spinal cord), it may be desirable to control the shape of the AP generating neural region of the spinal cord in order to prevent the generation of APs in non-target neural fibers. For example, to produce the feeling of paresthesia without inducing involuntary motor movements within the patient, it is often desirable to preferentially stimulate nerve fibers in the dorsal column (DC nerve fibers), which primarily include sensory nerve fibers, over nerve fibers in the dorsal roots (DR nerve fibers), which include both sensory nerve fibers and motor reflex nerve fibers. While DC nerve fibers are the intended targets in conventional SCS, in fact, the DR nerve fibers often are recruited first because of geometric, anatomical, and physiological reasons. For example, the DR nerve fibers have larger diameters than the largest nearby DC nerve fibers, and thus, have a lower threshold at which they are excited. Other factors that contribute to the lower threshold needed to excite DR nerve fibers are the different orientations of the DC nerve fibers and DR nerve fibers, the curved shape of the DR nerve fibers, and the inhomogeneity and anisotropy of the surrounding medium at the entrance of the DR nerve fibers into the spinal cord. Thus, DR nerve fibers may still generate APs at lower voltages than will nearby DC nerve fibers. As a result, the DC nerve fibers that are desired to be stimulated have a lower probability to be stimulated than do the DR nerve fibers, and thus, the reflex motor nerve fibers intermingled among the sensor nerve fibers of a dorsal root are often recruited, leading to discomfort or muscle twitching, thereby preventing satisfactory paresthesia coverage.

For reasons such as these, it is often desirable to modify the threshold at which neural tissue is activated in a manner that maximizes excitation of the target neural tissue, while minimizing excitation of the non-target neural tissue; that is, to increase the DR/DC threshold ratio. This can be accomplished by sinking an electrical pulse to a cathodic electrode located at the center of the spinal cord to depolarize the target tissue adjacent the cathodic electrode, thereby creating APs along the DC nerve fibers, while an electrical pulse can be sourced to anodic electrodes on both sides of the cathodic electrode to hyperpolarize non-target tissue adjacent the anodic electrodes, thereby increasing the threshold of the DR nerve fibers.

As another example, in the case where the electrode array is rostro-caudally aligned (i.e., the electrodes are arranged along the neural fibers of the spinal cord), it may be desirable to induce APs in a bundle of target nerve fibers, and to the extent that APs are induced in bundle of non-target nerve fibers, block APs within the non-target nerve fibers from reaching the brain or any other parts of the nervous system. In particular, an electrical pulse can be sunk to a cathodic electrode to depolarize target tissue adjacent the cathodic electrode, thereby creating APs along a first bundle of nerve fibers, while an electrical pulse can be sourced to one or more anodic electrodes above or below the cathodic electrode to hyperpolarize non-target tissue adjacent the anodic electrode(s), thereby blocking any APs along a second bundle of nerve fibers that were inadvertently induced by the sink electrical pulse of the cathodic electrode.

Because the amount of electrical current that is sourced must equal the amount of electrical current that is sunk, the amount of sourced electrical current must be limited in order to minimize the adverse effects that could potentially occur as a result of the increased amount of the sunk electrical current. For example, in the previously described case where the electrode array is rostro-caudally aligned, an increase in the electrical current sunk by the cathode as a result of an increase in the electrical current sourced by the anodes(s) may result in the generation of APs in non-target nerve fibers that are not blocked by the sourced electrical current. In the previously described case where the electrode array is medio-laterally aligned, an increase in the electrical current sunk by the cathode as a result of an increase in the electrical current sourced by the anodes may result in the generation of APs in non-target DC nerve fibers.

To limit the amount of current sunk by a cathode, it is known to redistribute some of the cathodic current to a large surface area, such as the case of the IPG. Such a technique is described in U.S. patent application Ser. No. 11/300,963, entitled "Apparatus and Methods for Stimulating Tissue," which is expressly incorporated herein by reference. By distributing the cathodic current to a surface area that has no, or very little, effect on the neural tissue, the magnitude of the electrical pulses sourced by the anodes can be increased while avoiding a commensurate increase in the magnitude of the electrical pulses sunk to the cathode that is adjacent the neural tissue. In this manner, any adverse effects that may otherwise occur as a result of an increase in the electrical current sunk to the cathodic electrode, and thus delivered through the neural tissue adjacent the cathodic electrode, can be minimized.

While this electrical current redistribution technique is beneficial, it can only be implemented within an IPG that has independent current or voltage sources for the electrodes. That is, an IPG with a single current or voltage source provides no means for redistributing a selected amount of cathode current to the IPG case. Furthermore, inadvertent stimulation of tissue in the pocket in which the neurostimulator is implanted may occur. This pocket stimulation problem is exacerbated when a microstimulator, which is an implantable neurostimulator in which the body or case of the device is compact (typically on the order of a few millimeters is diameter by several millimeters to a few centimeters in length), is used to deliver energy to the stimulation lead. Because the case of a microstimulator is relatively small, the current density on the surface of the case may be quite high when the microstimulator is operated in a monopolar mode. As a result, undesired and perhaps annoying or painful stimulation in the implantation pocket might be expected.

There, thus, remains a need for an alternative neurostimulation method and system that minimizes any adverse effects that may result in an increase in cathodic current when the anodic current is increased.

SUMMARY OF THE INVENTION

In accordance with a first aspect of the present inventions, a method of providing therapy to a patient is provided. The method comprises implanting a plurality of electrodes within the patient. The method further comprises delivering a plurality of first electrical pulses to a first set of the electrodes, delivering at least a second electrical pulse to a second set of the electrodes to therapeutically stimulate the tissue of the patient during the deliverance of each of the first electrical pulses, and delivering at least a third electrical pulse (which may or may not therapeutically stimulate the tissue) to a third set of the electrodes during the deliverance of each of the first electrical pulses. The first electrical pulses have a first polarity, and each of the second electrical pulse(s) and third electrical pulses(s) has a second polarity opposite to the first polarity. For example, the first electrical pulses may be anodic, and the second and third electrical pulses may be cathodic. The second and third electrical pulses are temporarily offset from each other.

In one method, the second and third electrical pulses do not temporarily intersect at all. In another method, the magnitudes of the second electrical pulse(s) and the third electrical pulse(s) are equal. In still another method, the widths of the second electrical pulses(s) and the third electrical pulses(s) are equal. Another method comprises delivering at least a fourth electrical pulse having the second polarity to a fourth set of the electrodes during the deliverance of each of the first electrical pulses, wherein the second, third, and fourth electrical pulses are temporarily offset from each other.

The tissue to which the electrodes are placed adjacent can be, e.g., spinal cord tissue. In one method, the electrodes are arranged medio-laterally along the spinal cord tissue. In this case, the second electrode set can be adjacent to dorsal column neural fibers of the spinal cord tissue, the first electrode set can be adjacent to dorsal root neural fibers of the spinal cord tissue, the second electrical pulse(s) can generate action potentials in the dorsal column neural fibers of the spinal cord tissue, and the first electrical pulses can increase the action potential threshold of the dorsal root neural fibers. In another exemplary method, the electrodes are arranged rostro-caudally along the spinal cord tissue. In this case, the second electrode set can be a first distance from a first neural fiber bundle and a second greater distance from a second neural fiber bundle, the second electrical pulse(s) can generate action potentials in the first and second neural fibers bundles, and the first electrical pulses can block at least some of the action potentials in the first neural fiber bundle.

In accordance with a second aspect of the present inventions, a neurostimulation system is provided. The system comprises a plurality of electrical terminals configured for being respectively coupled to a plurality of electrodes, and analog output circuitry configured for delivering electrical pulses to the electrical terminals. The system further comprises control circuitry configured for controlling the analog output circuitry to deliver a plurality of first electrical pulses to a first set of the electrical terminals, to deliver at least a second electrical pulse having a second polarity opposite to the first polarity to a second set of the electrical terminals during the deliverance of each of the first electrical pulses, and to deliver at least a third electrical pulse having the second polarity to a third set of the electrical terminals during the deliverance of each of the first electrical pulses. In the same manner described above, the first electrical pulses have a first polarity, each of the second electrical pulse(s) and third electrical pulses(s) has a second a second polarity opposite to the first polarity, and the second and third electrical pulses are temporarily offset from each other.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG) or similar electrical stimulator, which may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Figure 1:
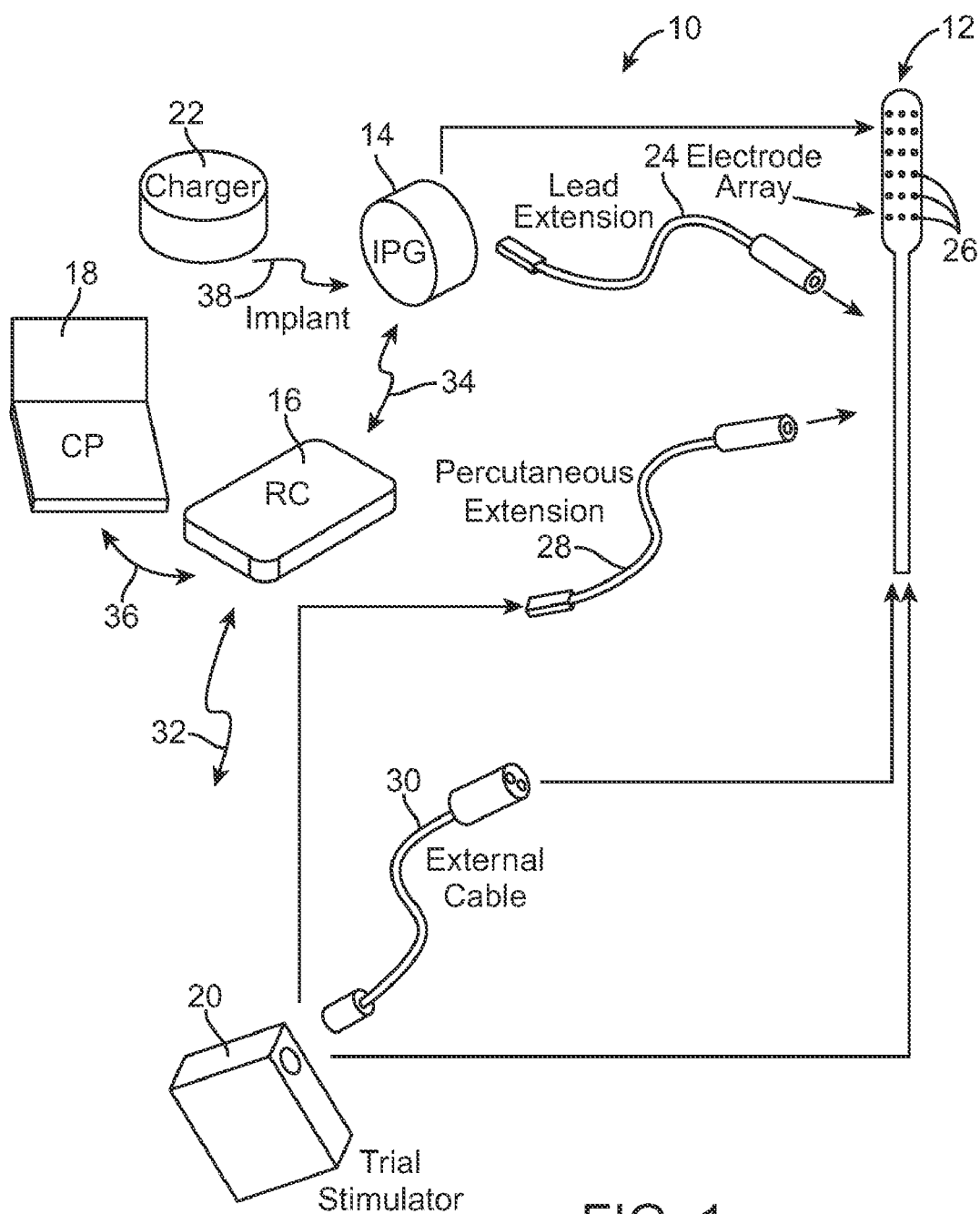
FIG. 1 is plan view of one embodiment of a spinal cord stimulation (SCS) system arranged in accordance with the present inventions.

Turning first to FIG. 1, an exemplary SCS system 10 generally comprises at least one implantable stimulation lead 12, an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the stimulation lead 12, which carries a plurality of electrodes 26 arranged in an array. The stimulation lead 12 is illustrated as a surgical paddle lead in FIG. 1, although as will be described in further detail below, one or more percutaneous stimulation leads can be used in place of the surgical paddle lead 12. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the effectiveness of the stimulation that is to be provided.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The external charger 22 is a portable device used to transcutaneously charge the IPG 14 via an inductive link 38.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
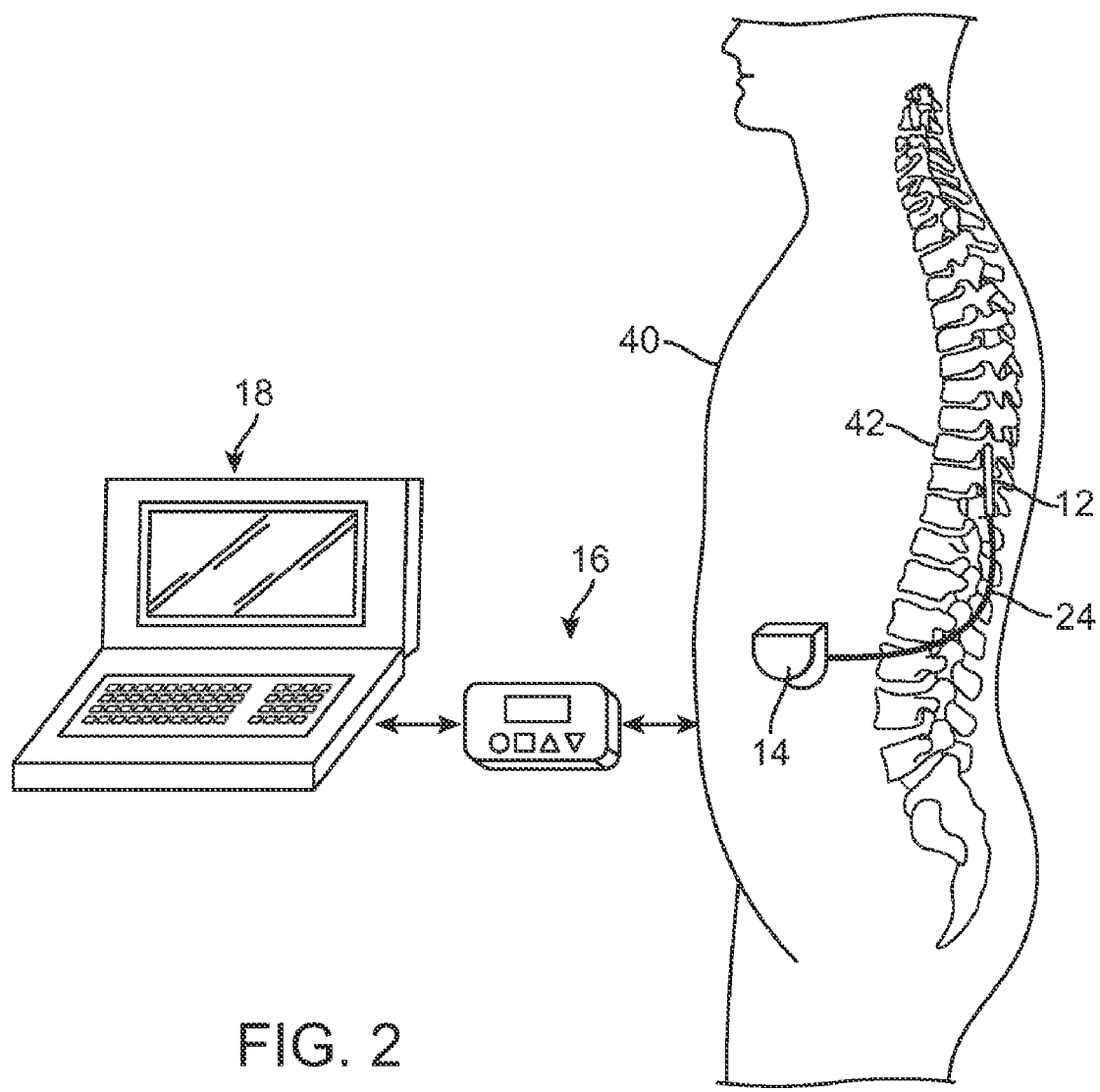
FIG. 2 is a plan view of the SCS system of FIG. 1 in use with a patient.

As shown in FIG. 2, the electrode lead 12 is implanted within the spinal column 42 of a patient 40. The preferred placement of the electrode lead 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
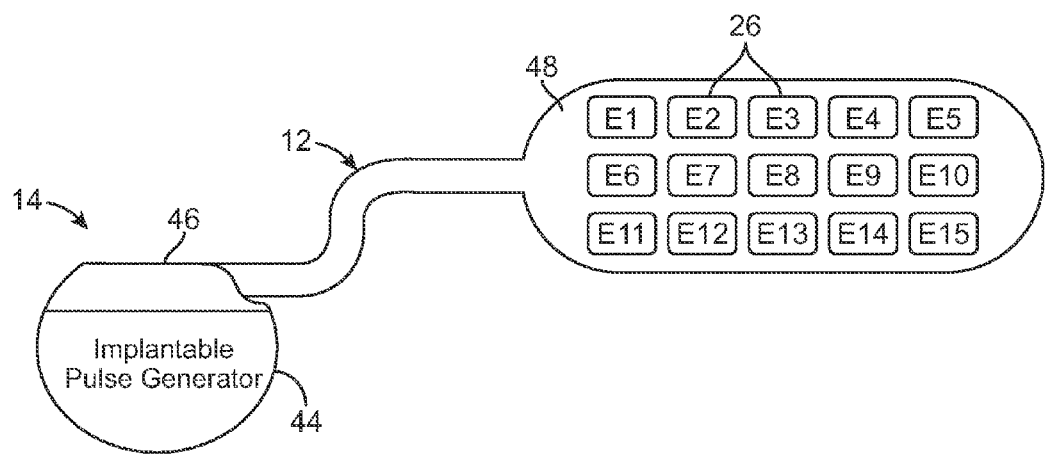
FIG. 3 is a plan view of an implantable pulse generator (IPG) and one embodiment of a stimulation lead used in the SCS system of FIG. 1.

Referring to FIG. 3, the IPG 14 comprises an outer case 44 for housing the electronic and other components (described in further detail below), and a connector 46 to which the proximal end of the stimulation lead 12 mates in a manner that electrically couples the electrodes 26 to the internal electronics (described in further detail below) within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

In the embodiment illustrated in FIG. 3, the surgical paddle lead 12 includes an elongated cylindrical lead body 46 and a distally-located paddle 48 with one side on which the electrodes 26 (in this case, electrodes E1-E15) are carried. The electrodes 26 are arranged in a two-dimensional array in three columns along the axis of the stimulation lead 12. In the illustrated embodiment, six rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

Figure 4:
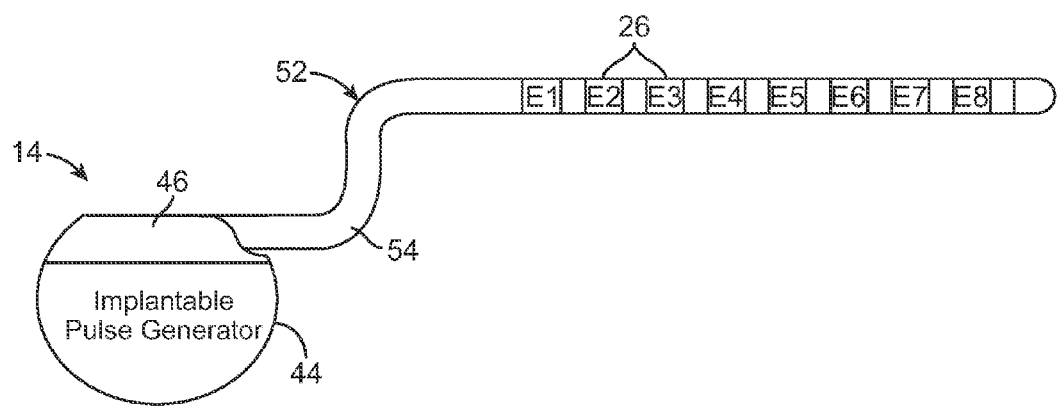
FIG. 4 is a plan view of an implantable pulse generator (IPG) and another embodiment of a stimulation lead used in the SCS system of FIG. 1.

In an alternative embodiment illustrated in FIG. 4, a percutaneous stimulation lead 52 can be used in the SCS system 10 instead of the surgical paddle lead 12. Although only one percutaneous stimulation lead 52 is shown, multiple percutaneous stimulation leads (e.g., two), can be used with the SCS system 10. The percutaneous stimulation lead 52 comprises an elongated cylindrical lead body 54, and the electrodes 26 take the form of ring electrodes mounted around the lead body 54. In the illustrated embodiment, the stimulation lead 52 has eight electrodes 26 (in this case, electrodes E1-E8). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation phase and an anodic (positive) recharge phase that is generated after the stimulation phase to prevent direct current charge transfer through the tissue, thereby avoiding electrode degradation and cell trauma. That is, charge is delivered through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Notably, as discussed in the background of the invention, there may be certain scenarios where it is desirable to increase the magnitude of electrical current at an anode or anodes without increasing the intensity of the stimulation provided by a cathode or cathodes. Significantly, the system 10 is capable of attenuating the stimulation intensity at a cathode by spreading a certain portion of the cathodic current on other electrodes with a "spatial-temporal spreading technique." In particular, cathodic current is temporally segmented into multiple short pulse widths that are transferred on other electrodes with different timing. The spatial-temporal spreading of the cathodic current can be between stimulation cathodes or between stimulation cathodes and non-stimulation ("non-therapeutic") electrodes.

Figure 5:
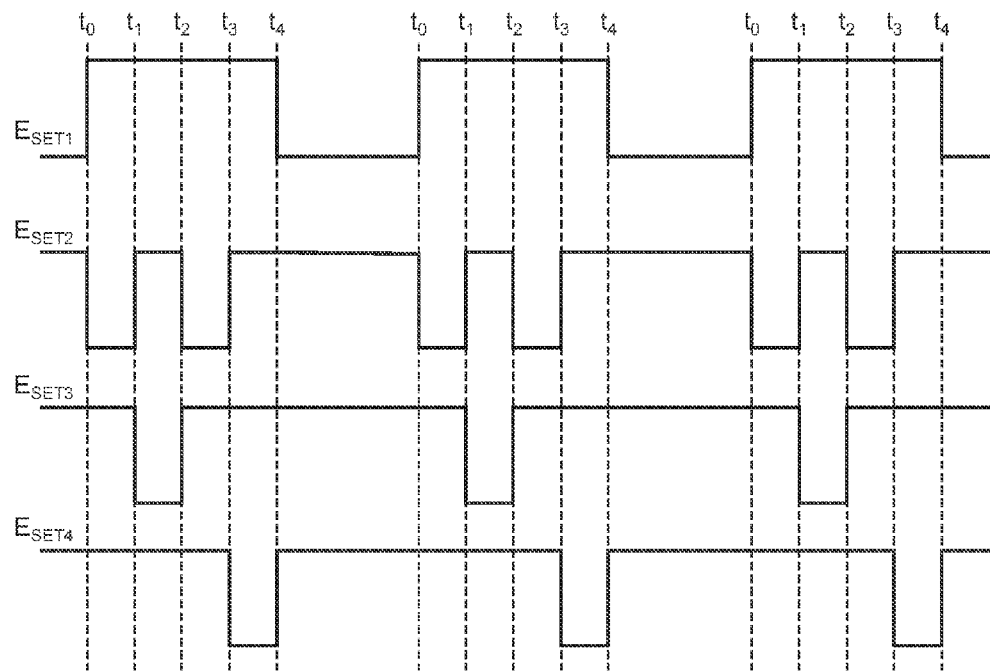
FIG. 5 is a timing diagram of a first technique used by the SCS system of FIG. 1 to deliver electrical pulses to different sets of electrodes.

Referring to FIG. 5, one example of a spatial-temporal spreading technique will now be described. As there shown, a series of anodic electrical pulses are delivered to a first set of electrodes $E_{SET1}$. During the delivery of each anodic electrical pulse, a plurality of cathodic electrical pulses (in this case, two) is delivered to a second set of electrodes $E_{SET2}$, a single cathodic electrical pulse is delivered to a third set of electrodes $E_{SET3}$, and a single cathodic electrical pulse is delivered to a fourth set of electrodes $E_{SET4}$. Notably, each set of electrodes may include any number of electrodes, including one electrode.

In the illustrated embodiment, the cathodic electrical pulses that are delivered to the second electrode set $E_{SET2}$ therapeutically stimulate the nerve tissue adjacent these electrode(s) due to the combined duration and close proximity of the pulses. In contrast, the single, short, cathodic pulse delivered to the third electrode set $E_{SET3}$ and the single, short, cathodic pulse delivered to the fourth electrode set $E_{SET4}$ do not therapeutically stimulate the nerve tissue adjacent these electrodes. Thus, in this case, the second electrode set $E_{SET2}$ are operated as therapeutic electrodes, and the third and fourth electrode sets $E_{SET3}$ and $E_{SET4}$ are operated as non-therapeutic electrodes.

Significantly, the cathodic electrical pulses are all temporarily offset from each other, thereby temporarily distributing the cathodic current that would otherwise be delivered to the second electrode set $E_{SET2}$ to the third and fourth electrode sets $E_{SET3}$ and $E_{SET4}$. In particular, each anodic electrical pulse is temporarily segmented into four time segments $t_0$-$t_1$, $t_1$-$t_2$, $t_3$-$t_4$, and $t_4$-$t_5$, with two cathodic electrical pulses being delivered to the first electrode set $E_{SET2}$ respectively during the first and third time segments $t_0$-$t_1$ and $t_3$-$t_4$, a single cathodic electrical pulse being delivered to the third electrode set $E_{SET2}$ during the second time segment $t_1$-$t_2$, and a single cathodic electrical pulse being delivered to the fourth electrode set $E_{SET2}$ during the fourth time segment $t_4$-$t_5$. As a result, the stimulation intensity of the nerve tissue adjacent the second electrode set $E_{SET2}$ will be decreased. As shown in FIG. 5, none of the cathodic electrical pulses temporarily intersect each other. In fact, because cathodic electrical current must be delivered to balance out the deliverance of the anodic electrical current, the next cathodic electrical pulse is initiated as soon as the currently delivered electrical pulse is terminated.

Figure 6:
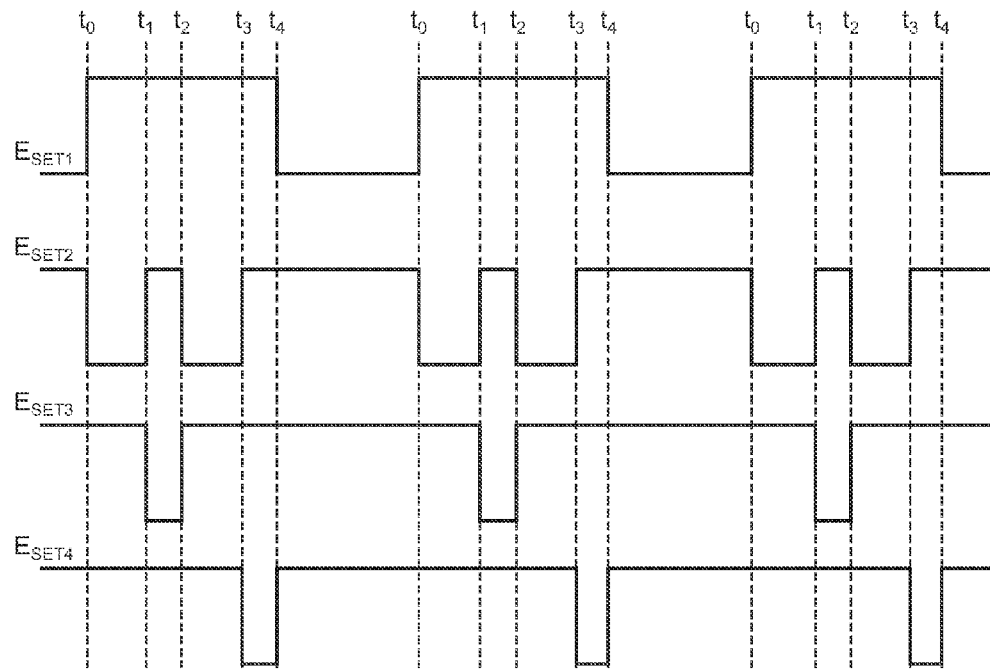
FIG. 6 is a timing diagram of a second technique used by the SCS system of FIG. 1 to deliver electrical pulses to different sets of electrodes.

Although the widths of the cathodic electrical pulses delivered to the second, third, and fourth electrode sets $E_{SET2}$, $E_{SET3}$, and $E_{SET4}$, and thus, the respective time segments $t_0$-$t_1$, $t_1$-$t_2$, $t_3$-$t_4$, and $t_4$-$t_5$, are shown as being equal in FIG. 5, the widths of these electrical pulses and time segments may be unequal, as shown in FIG. 6. As there shown, the width of each of the electrical pulses delivered to the second electrode set $E_{SET2}$ is greater than the width of each of the electrical pulses delivered to the third and fourth electrode sets $E_{SET3}$ and $E_{SET4}$. In this case, the stimulation intensity of the nerve tissue adjacent the second electrode set $E_{SET2}$ may not be decreased as much as that in the case illustrated in FIG. 5 due to the increased cathodic electrical pulse width.

Figure 7:
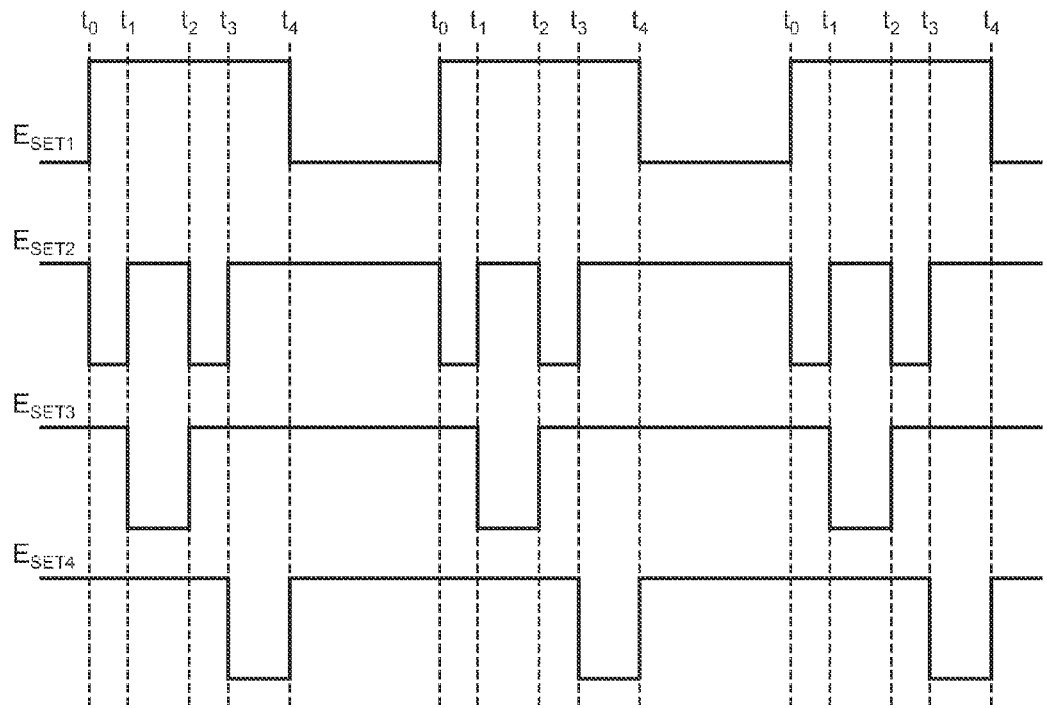
FIG. 7 is a timing diagram of a third technique used by the SCS system of FIG. 1 to deliver electrical pulses to different sets of electrodes.

Alternatively, as shown in FIG. 7, the width of each of the electrical pulses delivered to the second electrode set $E_{SET2}$ is less than the width of each of the electrical pulses delivered to the third and fourth electrode sets $E_{SET3}$ and $E_{SET4}$. In this case, the stimulation intensity of the nerve tissue adjacent the second electrode set $E_{SET2}$ may be further decreased relative to that in the case illustrated in FIG. 5 due to the decreased cathodic electrical pulse width. If it is preferred that the nerve tissue adjacent the third and fourth electrode sets $E_{SET3}$ and $E_{SET4}$ not be stimulated, the widths of the cathodic electrical pulses delivered to these electrode sets should be relatively small—albeit greater than the width of each of the cathodic electrical pulses delivered to the second electrode set $E_{SET2}$.

Figure 8:
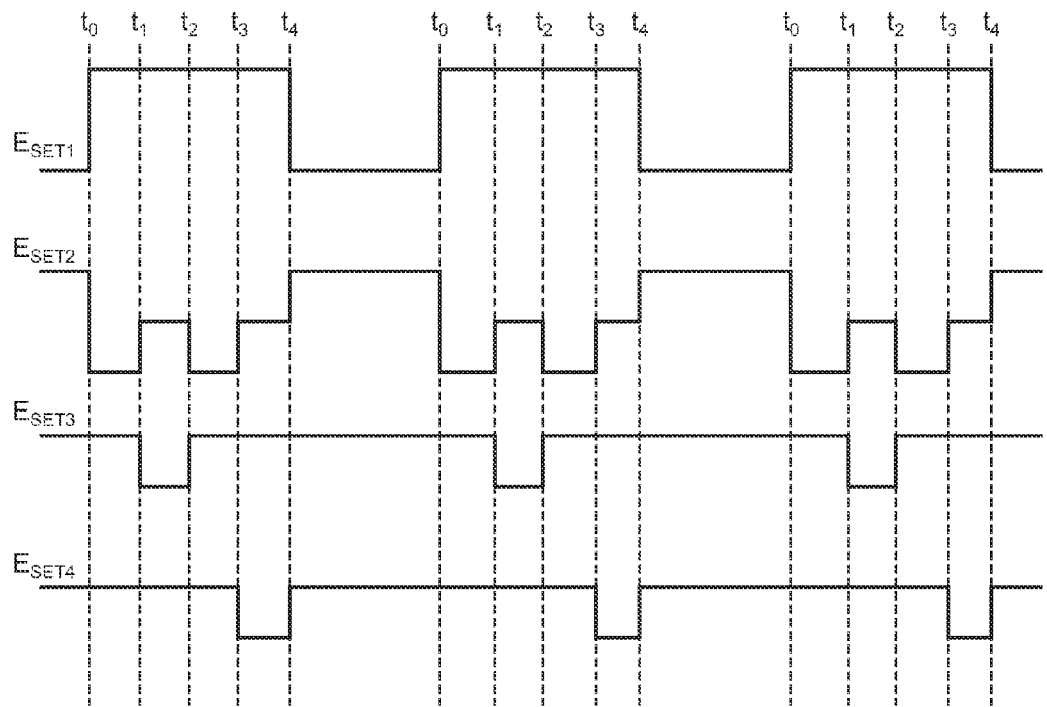
FIG. 8 is a timing diagram of a fourth technique used by the SCS system of FIG. 1 to deliver electrical pulses to different sets of electrodes.

As also shown in FIG. 5, the magnitudes of the cathodic electrical pulses are equal, and in fact, each contain the same amount of electrical energy, reflecting that fact that the cathodic electrical current must be conserved (assuming a uniform anodic electrical pulse) as it is temporarily shifted from one electrode set to another. Alternatively, as shown in FIG. 8, the cathodic electrical pulse delivered to the second electrode set $E_{SET2}$ may not be terminated, but rather decreased in magnitude. In this case, the magnitude of each of the cathodic electrical pulses delivered to the third and fourth electrode sets $E_{SET3}$ and $E_{SET4}$ will be equal to the decrease in magnitude of the cathodic electrical pulse delivered to the second electrode set $E_{SET2}$.

Figure 9:
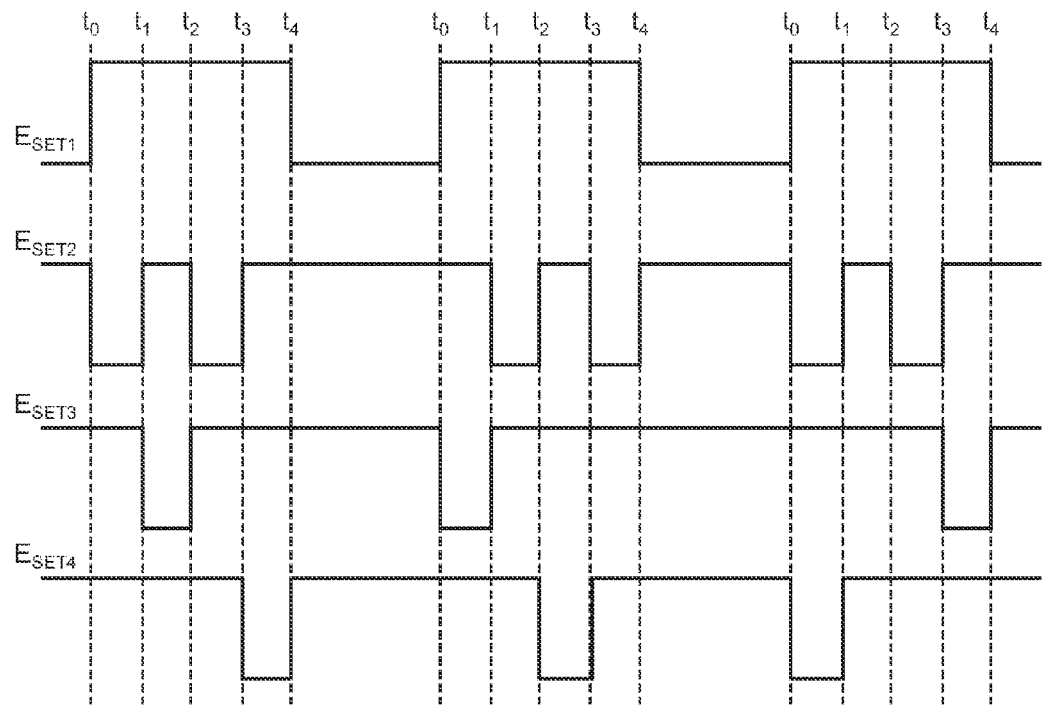
FIG. 9 is a timing diagram of a fifth technique used by the SCS system of FIG. 1 to deliver electrical pulses to different sets of electrodes.

Although the order of the cathodic electrical pulses delivered to electrode sets are illustrated in FIG. 5 as being regular (in this case, for each anodic electrical pulse, a cathodic electrical pulse is initially delivered to the second electrode set $E_{SET2}$, then fourth electrode set $E_{SET4}$), the order of the cathodic electrical pulses can be randomized, as illustrated in FIG. 9. While the two cathodic electrical pulses delivered to the second electrode set $E_{SET2}$ are closely spaced for each of the anodic electrical pulses to ensure stimulation of the nerve fibers adjacent the second electrode set $E_{SET2}$, the order of the anodic electrical pulses delivered to the respective electrode sets is randomized for each of the anodic electrical pulses. Alternatively, the cathodic electrical pulses may be delivered to the electrode sets in a regular, but non-uniform pattern.

Figure 10:
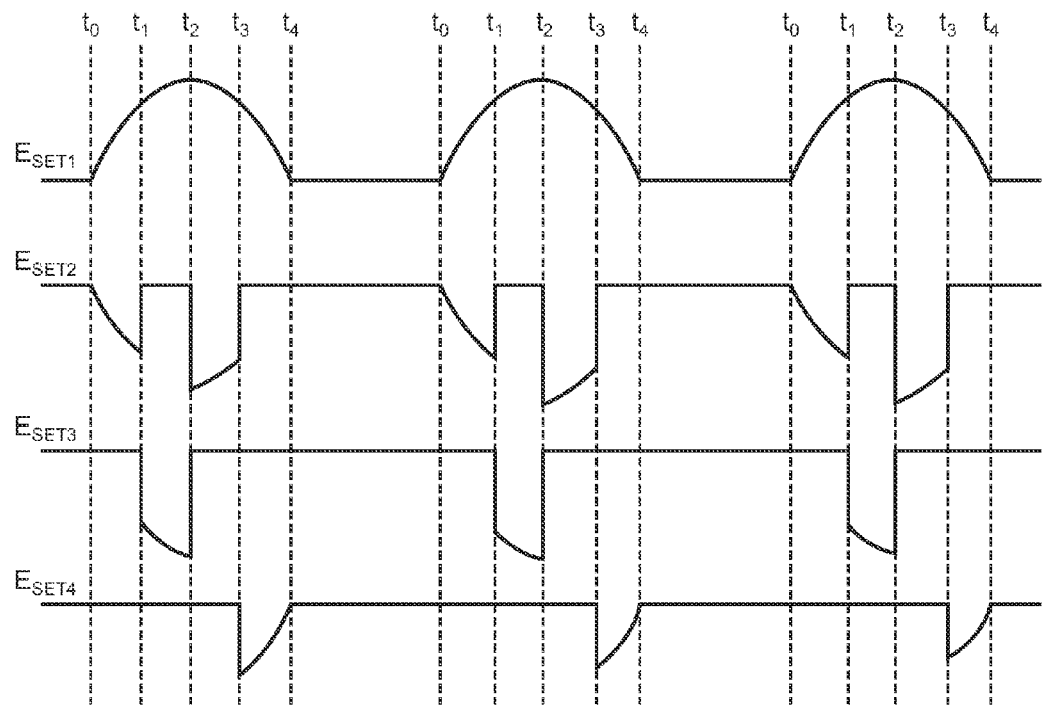
FIG. 10 is a timing diagram of a sixth technique used by the SCS system of FIG. 1 to deliver electrical pulses to different sets of electrodes.

Although the shape of the anodic and cathodic electrical pulses delivered to the respective electrode sets are shown as being square in FIG. 5, the electrical pulses can be any shape, including sinusoidal, exponential, logarithmic, trapezoidal, etc. For example, as shown in FIG. 10, the anodic electrical pulses are sinusoidal. In this case, to balance out the sinusoidal shape of each anodic electrical pulse, the cathodic electrical current must also be sinusoidal. As a result, the cathodic electrical pulses delivered to the electrode sets will have the shape illustrated in FIG. 10.

Figure 11:
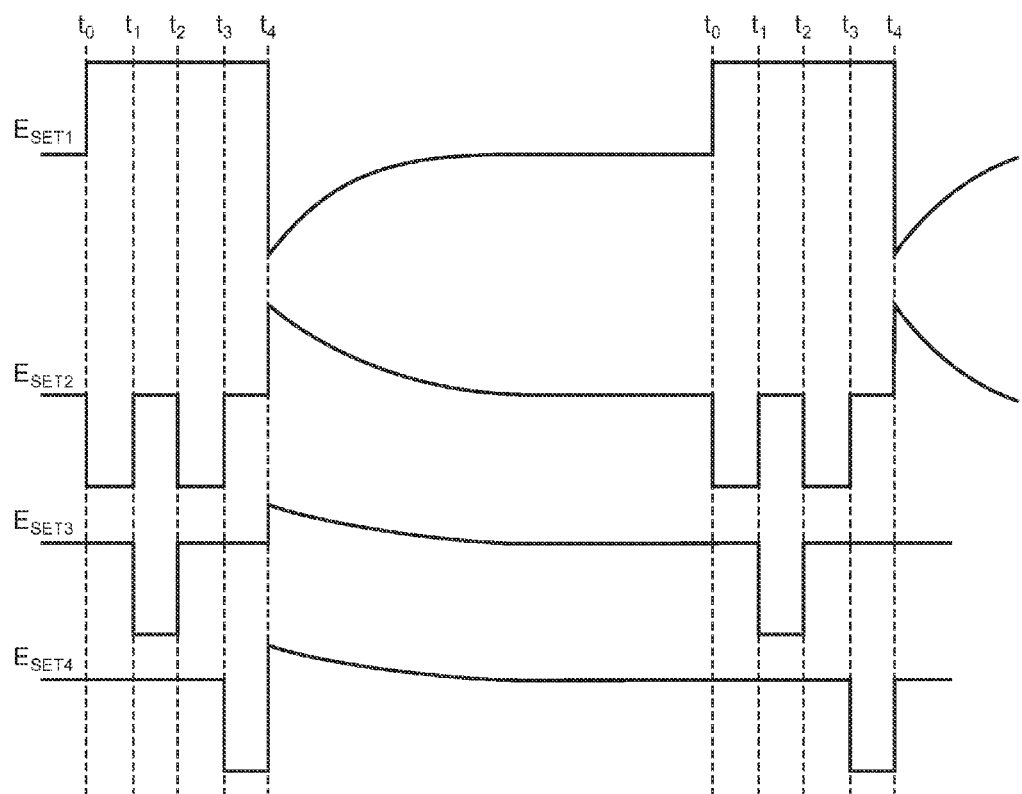
FIG. 11 is a timing diagram of a seventh technique used by the SCS system of FIG. 1 to deliver electrical pulses to different sets of electrodes.

It should also be noted that the electrical pulses are illustrated in FIG. 5 as being monophasic. In this case, where biphasic electrical pulses are used, the anodic electrical pulse will have a stimulation phase and a recharge phase, as shown in FIG. 11. During the stimulation phase of the anodic pulse, the ordering and characteristics of the cathodic electrical pulses delivered to the respective second, third, and fourth electrode sets $E_{SET2}$, $E_{SET3}$, and $E_{SET4}$ will be the same as that shown in FIG. 5. However, during the recharge phase of the anodic pulse (i.e., after time $t_4$), a corresponding and opposite recharge pulse is delivered to the electrode set $E_{SET2}$, $E_{SET2}$, and $E_{SET4}$, to recover the delivered charge from each electrode.

Figure 12:
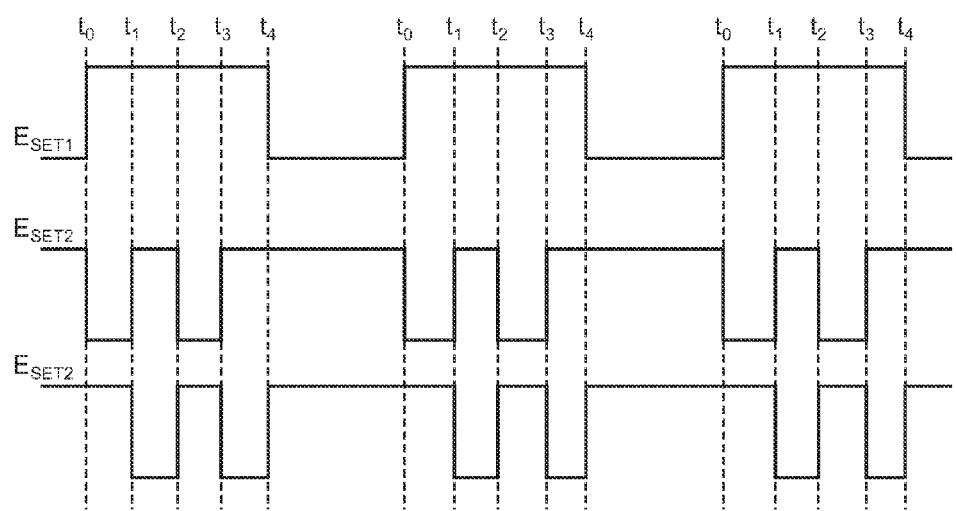
FIG. 12 is a timing diagram of an eighth technique used by the SCS system of FIG. 1 to deliver electrical pulses to different sets of electrodes.

Although the cathodic electrical pulses respectively delivered to some of the electrodes sets (in this case, the third and fourth electrode sets $E_{SET3}$ and $E_{SET34}$) are non-therapeutic, all of the electrode sets to which the cathodic electrical pulses are respectively delivered may be therapeutic. For example, as shown in FIG. 12, a plurality of cathodic electrical pulses (in this case, two) is delivered to a second set of electrodes $E_{SET2}$, and another plurality of cathodic electrical pulses (in this case, two) is delivered to a third set of electrodes $E_{SET3}$. Thus, as was the case in FIG. 5 with respect to the only stimulating electrode set to which the cathodic electrical pulses were delivered (i.e., the second electrode set $E_{SET2}$), the cathodic electrical pulses that are delivered to the respective second and third electrode sets $E_{SET2}$, $E_{SET3}$, therapeutically stimulate the nerve tissue adjacent these electrode sets due to the combined duration and close proximity of the pulses for each electrode set.

Figure 13:
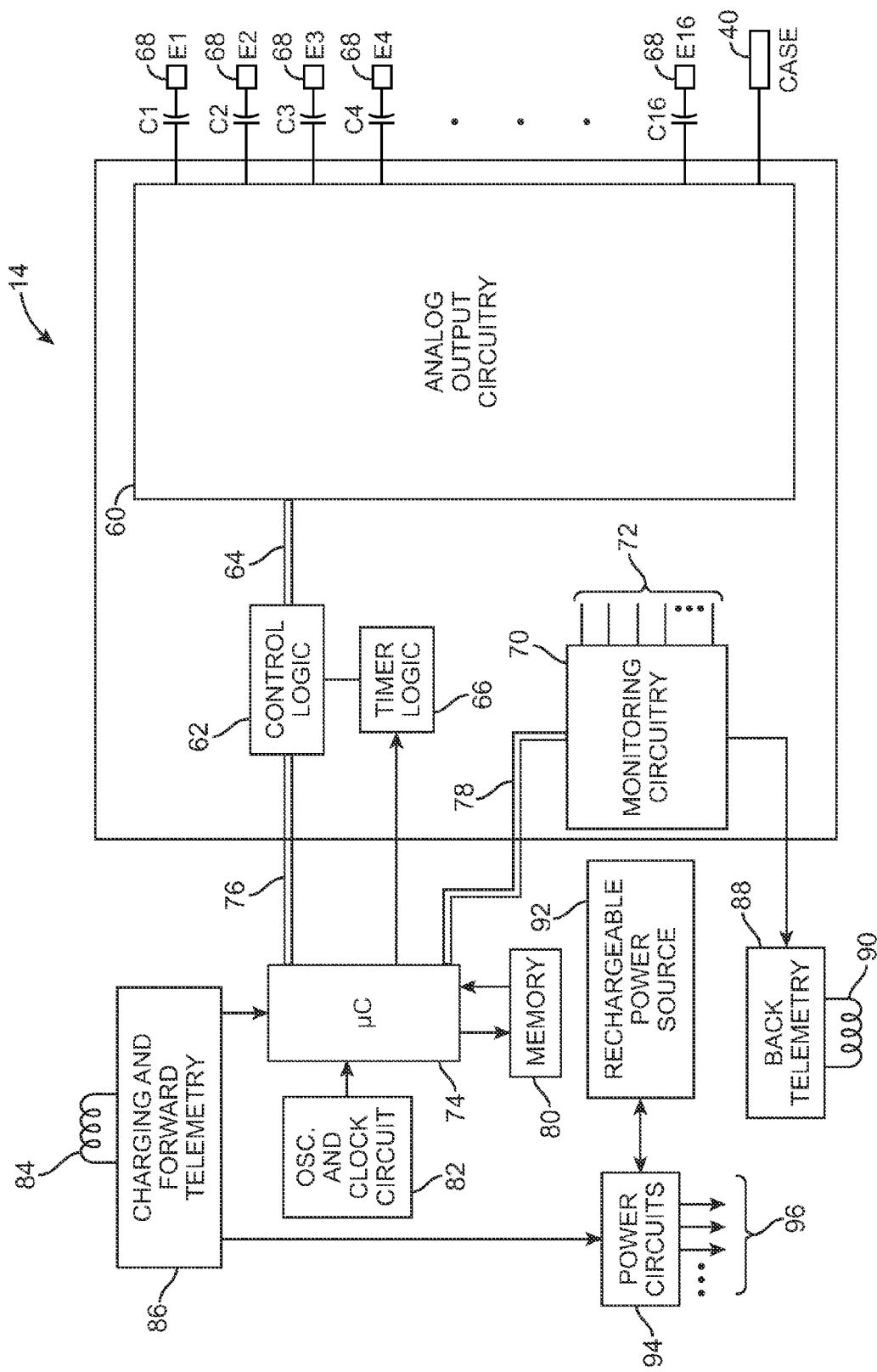
FIG. 13 is a block diagram of the internal components of the IPG of FIG. 3.

Turning next to FIG. 13, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference. The analog output circuitry 60 may also comprise pulse shaping circuitry (not shown) capable of shaping the pulses (e.g., a square pulse, an exponential pulse, a logarithmic pulse, a ramped pulse, a trapezoidal pulse, etc.). Further details discussing pulse shaping circuitry and the different pulse shapes that can be generated are disclosed in U.S. patent application Ser. No. 60/951,177, entitled "Use of Stimulation Pulse Shape to Control Neural Recruitment Order and Clinical Effect," which is expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (μC) 74 that controls the control logic 62 over data bus 76, and obtains status data from the monitoring circuitry 70 via data bus 78. The IPG 14 further comprises memory 80 and oscillator and clock circuit 82 coupled to the μC 74. The μC 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the μC 74 generates the necessary control and status signals, which allow the μC 74 to control the operation of the IPG 14 in accordance with a selected operating program and stimulation parameters. In controlling the operation of the IPG 14, the μC 74 is able to individually generate stimulus pulses at the electrical terminals 68 using the analog output circuitry 60, in combination with the control logic 62 and timer logic circuitry 66, thereby allowing each electrical terminal 68 (and thus, each electrode 26) to be paired or grouped with other electrical terminals 68 (and thus, other electrodes 26), including the monopolar case electrode, to control the polarity, amplitude, rate, pulse width, pulse shape, burst rate, and channel through which the current stimulus pulses are provided. The μC 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above with respect to FIG. 2, the stimulation lead 12 (or alternatively, the stimulation lead 52) is implanted within the spinal column 42 adjacent the spinal cord area to be stimulated. The electrodes 26 may be arranged medio-laterally with respect to the spinal cord, or alternatively, the electrodes 26 may be arranged rostro-caudally with respect to the spinal cord.

Figure 14:
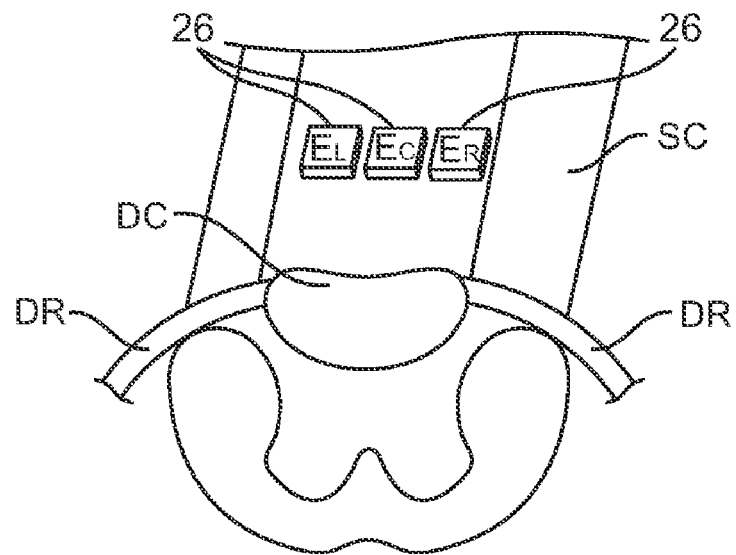
FIG. 14 is a perspective view of the electrodes of the stimulation lead of FIG. 3 medio-laterally located over the spinal cord of a patient.
Figure 15:
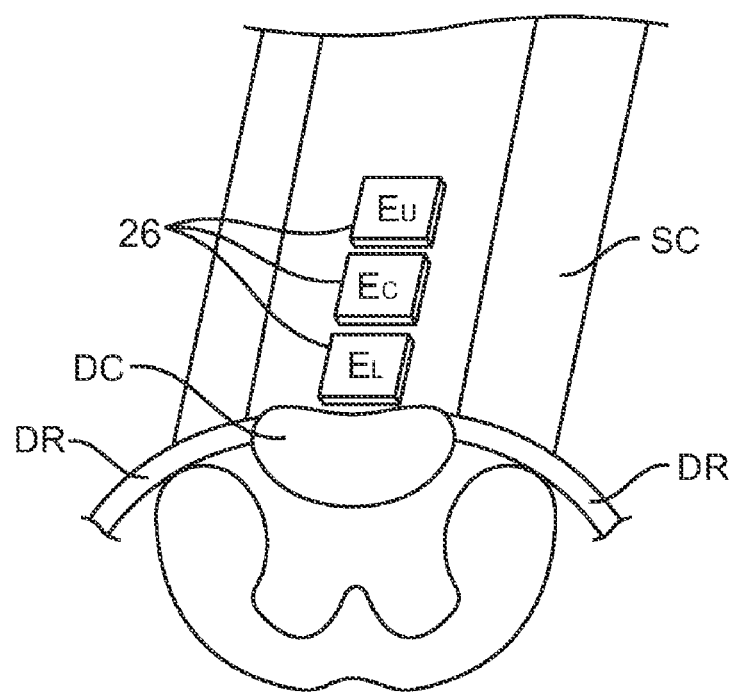
FIG. 15 is a perspective view of the electrodes of the stimulation lead of FIG. 4 rostro-caudally located over the spinal cord of a patient.

For example, as shown in FIG. 14, the surgical lead 12 illustrated in FIG. 2 can be used to arrange three electrodes 26 (one center electrode $E_C$ located over the center of the dorsal column DC nerve fibers, a left electrode $E_L$ laterally placed from the center of the DC nerve fibers adjacent the left dorsal root DR nerve fibers, and a right electrode $E_R$ laterally placed from the center of the dorsal column DC nerve fibers adjacent the right dorsal root DR nerve fibers) transverse to the axis of the spinal cord SC (medio-laterally). As another example, as shown in FIG. 15, the percutaneous lead 52 illustrated in FIG. 3 can be used to arrange three electrodes 26 (an upper (or rostral) electrode $E_U$, a center electrode $E_C$, and a lower (or caudal) electrode $E_L$) along the axis of the spinal cord SC (rostro-caudally) over the dorsal column DC nerve fibers. The system 10 has application in a wide variety of SCS regimens.

Figure 17:
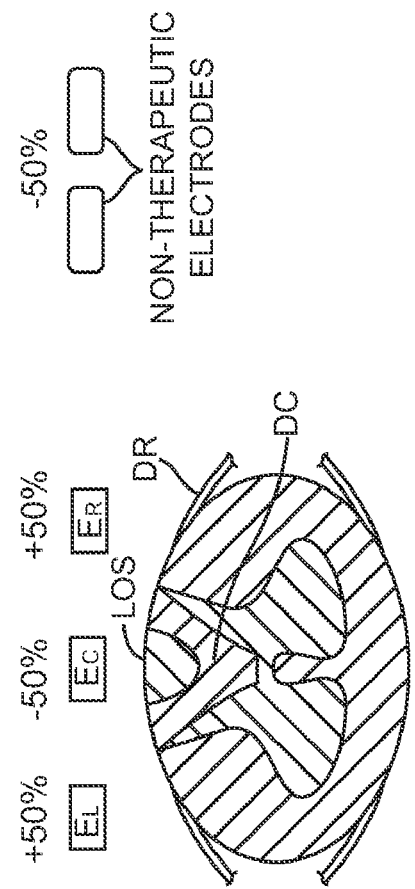
FIG. 17 is a cross-section diagram of a spinal cord, particularly illustrating a locus of stimulation induced by the medio-lateral electrode arrangement of FIG. 14.
Figure 16:
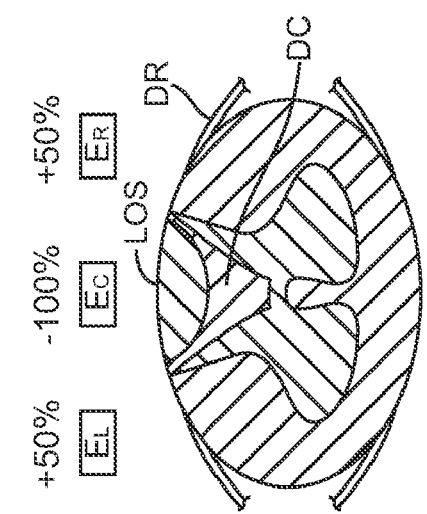
FIG. 16 is a cross-section diagram of a spinal cord, particularly illustrating a locus of stimulation induced by a prior art medio-lateral electrode arrangement.

For example, neurostimulation regimens that use the surgical paddle lead 12 to medio-laterally arrange the electrodes 26 in the manner illustrated in FIG. 14 can be used to shape of the AP generating neural region of the spinal cord in order to prevent the generation of APs in non-target neural fibers. As shown in FIGS. 16 and 17, the center electrode $E_C$ is placed over the dorsal column DC nerve fibers, while the left electrode $E_L$ and the right electrode $E_R$ are respectively placed over the dorsal root DR nerve fibers on both sides of the dorsal column DC nerve fibers.

A conventional SCS regimen that sinks all of the electrical current within the stimulation lead(s) implanted within the spinal column will serve as a reference for the stimulation regimens performed in accordance with the present inventions, and will thus be initially described with reference to FIG. 16. In this conventional stimulation regimen, the left and right electrodes $E_L$ and $E_R$ are activated as anodes and the center electrode $E_C$ is activated as a cathode. In the illustrated embodiment, the two electrodes $E_L$, $E_R$ are each sourcing 50% of the total current (e.g., 2 mA each), and the center electrode $E_C$ is sinking 100% of the total current (e.g., 4 mA). The combination of the hyperpolarizing electric fields generated by the left and right electrodes $E_L$, $E_R$ and the depolarizing electric field generated by the center electrode $E_C$ results in an area within the dorsal column DC that is at or above the depolarization threshold. This area, which has an overall depth and width, is the locus of stimulation LOS.

In the conventional stimulation regimen described above, it is desirable that the locus of stimulation LOS be as narrow as possible without increasing the depth of the LOS, thereby stimulating target nerve fibers within the dorsal column DC, while preventing stimulation of non-target nerve fibers within the dorsal roots DR. This would require an increase in the hyperpolarizing electrical field generated by the left and right electrodes $E_L$, $E_R$ over that illustrated in FIG. 16. That is, strengthening of the hyperpolarizing electric fields created by the electrodes $E_L$, $E_R$ tends to result in a narrowing of the locus of stimulation LOS, because it weakens the lateral edges of the depolarizing electric field created by the center electrode $E_C$. However, this necessarily may result in an increase in the current sunk by the center electrode $E_C$, thereby increasing the depth of the locus of stimulation LOS, which may lead to undesirable outcomes (e.g., discomfort or undesirable reflexive activity).

The system 10 may be used to solve this problem by effectively increasing the AP threshold of the dorsal root DR nerve fibers relative to the AP threshold of the dorsal column DC nerve fibers. As illustrated in FIG. 17, one example of a stimulation regimen in accordance with a present invention involves creating a locus of stimulation LOS that has a smaller width and the same depth. Here, in the same manner described above with respect to FIG. 16, the left and right electrodes $E_L$, $E_R$ are activated as anodes and the center electrode $E_C$ is activated as a cathode. However, the amount of current sourced at the left and right electrodes $E_L$, $E_R$ should be sufficient to create a hyperpolarizing electric field that is strong enough to narrow the locus of stimulation LOS to the smaller width. For example, the current sourced at the left and right electrodes $E_L$, $E_R$ may be increased (e.g., 4-8 mA each) in order to strengthen the hyperpolarizing electric fields.

Notably, sinking all of the current sourced by the left and right electrodes $E_L$, $E_R$ into the center electrode $E_C$ could result in a depolarizing electric field that would undesirably increase the depth of the locus of stimulation LOS. In this case, however, a portion of the current sourced by the left and right electrodes $E_L$, $E_R$ is sunk into other electrodes 26 of the stimulation lead 12. That is, the cathodic electrical current is temporarily distributed between the center electrode $E_C$ and other electrodes in accordance with, e.g., the temporal segmentation techniques illustrated in FIGS. 5-12. In the case of the technique illustrated in FIG. 5, the cathodic electrical current is temporarily distributed between the center electrode $E_C$ and non-therapeutic electrodes, with 50% of the cathodic electrical current being delivered to the center electrode $E_C$, and the remaining 50% of the cathodic electrical current being delivered to the non-therapeutic electrodes.

As a result, only a portion of the current sourced by the left and right electrodes $E_L$, $E_R$ is sunk into the center electrode $E_C$, thereby allowing the intensity of the depolarizing electric field created by the center electrode $E_C$ to be reduced to a level that does not increase the depth of the locus of stimulation LOS compared to that illustrated in FIG. 16. Thus, the electrical current sunk at the center electrode $E_C$ provides therapy to the bodily region (i.e., the dermatome) corresponding to the stimulated portion of the spinal cord, and in this case, the upper leg regions, while the electrical current concurrently sunk at the peripheral electrode(s) provides therapy to the peripheral region, and in this case, the lower back region.

Alternatively, rather than narrowing the locus of stimulation LOS in both directions, the locus of stimulation LOS may be narrowed in only one direction. Here, only one of left and right electrodes $E_L$, $E_R$ is activated as an anode. In this case, 100% of the total current is being sourced at the left electrode $E_L$ or right electrode $E_R$, while the current is being sunk at the center electrode $E_C$ and peripheral electrodes.

Figure 18:
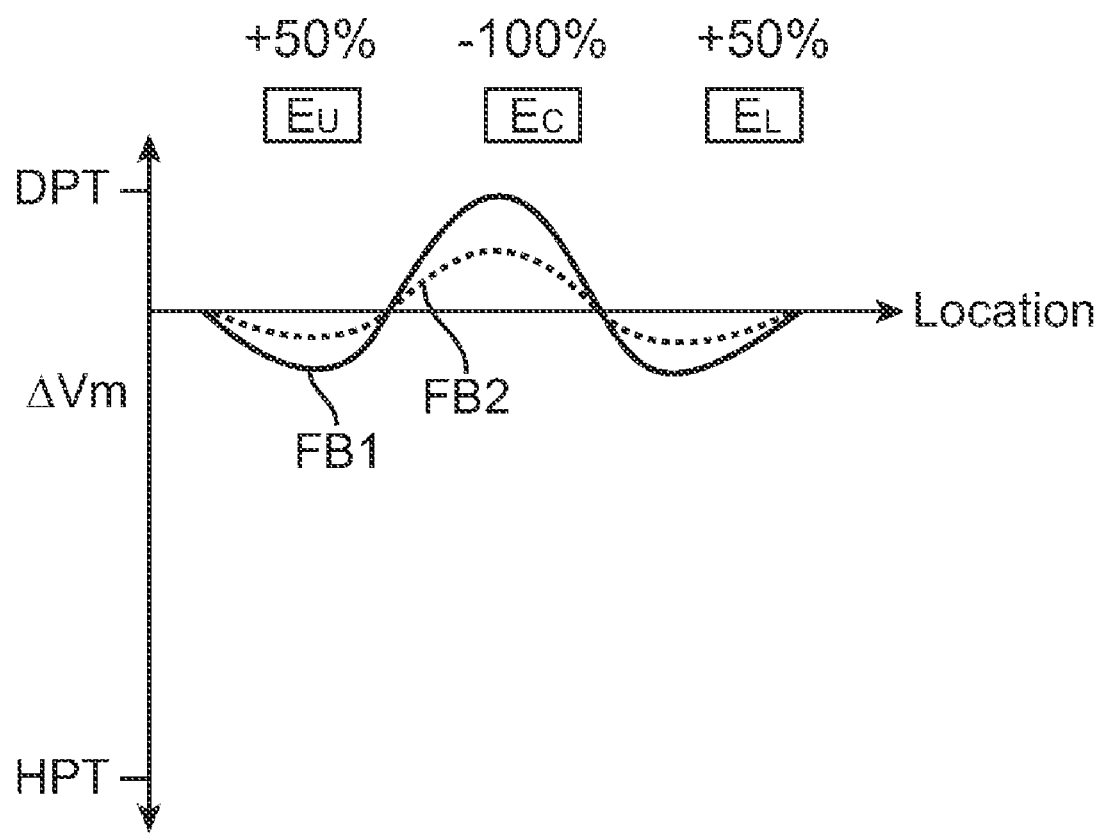
FIG. 18 is a graph of the changes in neural fiber transmembrane potential in first and second fibers bundles induced by a prior art rostro-caudal electrode arrangement.
Figure 19:
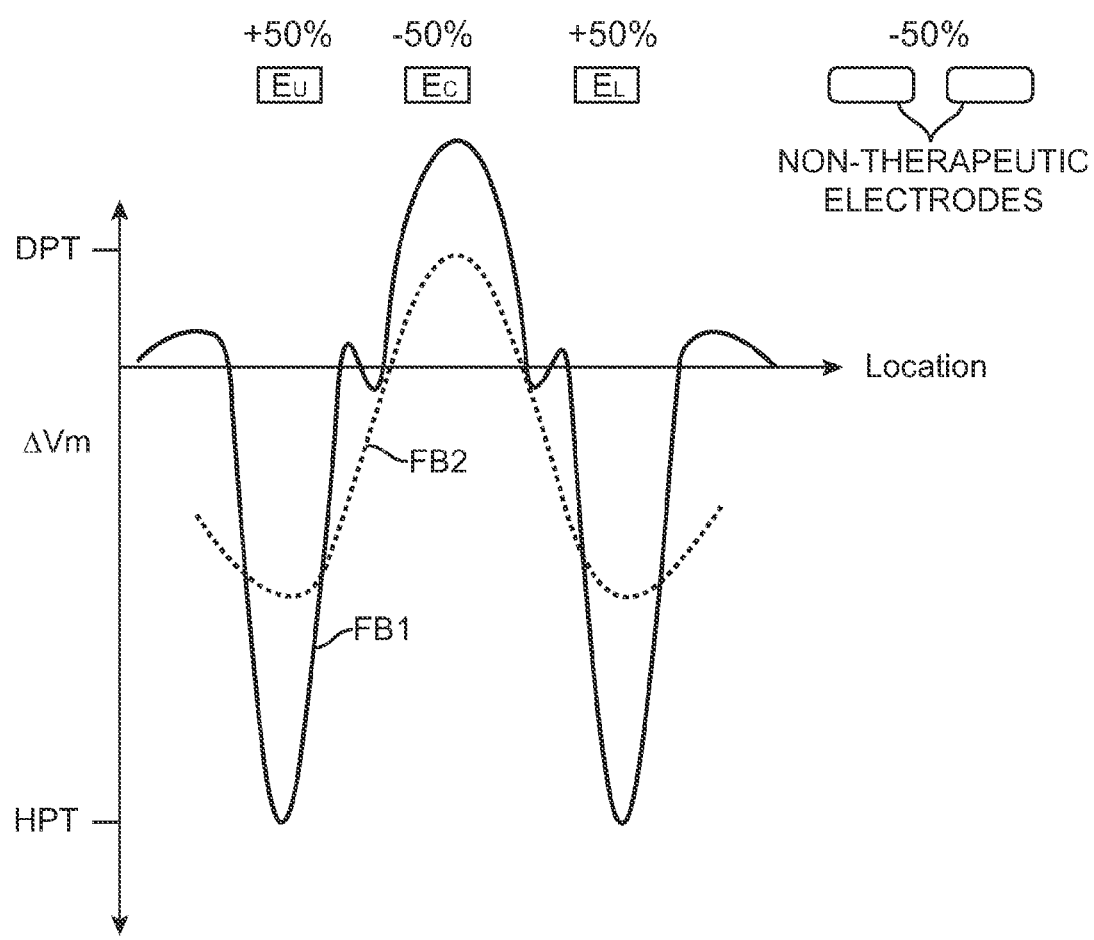
FIG. 19 is a graph of the changes in neural fiber transmembrane potential in first and second fibers bundles induced by the rostro-caudal electrode arrangement of FIG. 15.

As another example, neurostimulation regimens that use one percutaneous lead 52 to rostro-caudally arrange the electrodes 26 can be used to selectively block APs in neural fibers. As shown in FIGS. 18 and 19, the changes in transmembrane potential ($\Delta V_m$) of neural fibers in fiber bundles that are in the vicinity of the electrodes 26 are graphically illustrated when electric fields are generated by the electrodes 26 during the neurostimulation regimens. The neurostimulation regimens are discussed in the context of first and second fiber bundles FB1 and FB2. In the illustrated examples, the first fiber bundle FB1 is the closest fiber bundle to the electrodes 56, and the second fiber bundle FB2 is the next closest fiber bundle to the electrodes 56.

A conventional SCS regimen that sinks all of the electrical current within the stimulation lead implanted within the spinal column will serve as a reference for the stimulation regimens performed in accordance with the present inventions, and will thus be initially described with reference to FIG. 18. In this conventional stimulation regimen, the upper and lower electrodes $E_U$, $E_L$ are activated as anodes, and the center electrode $E_C$ is activated as a cathode. In the illustrated embodiment, 50% of the total current (e.g., 2 mA) is being sourced at each of the upper and lower electrodes $E_U$, $E_L$, and 100% of the total current (e.g., 2 mA) is being sunk at the center electrode $E_C$.

The depolarizing electric field generated by the center electrode $E_C$ is sufficient to create APs in some of the neural fibers in the first fiber bundle FB1. In other words, the depolarization threshold DPT has been met for the first fiber bundle FB1 in the tissue adjacent the center electrode $E_C$. The depolarizing electric field generated by the center electrode $E_C$ is substantially weaker at the second fiber bundle FB2 and is below the AP-creating depolarization threshold DPT. The locus of stimulation is, therefore, defined by the portion of the depolarizing electric field generated by the center electrode $E_C$ that is at or above the depolarization threshold DPT.

The upper and lower electrodes $E_U$, $E_L$, which are functioning as anodes in the stimulation regimen illustrated in FIG. 18, will create hyperpolarizing electric fields in the neural tissue adjacent the upper and lower electrodes $E_U$, $E_L$. When the electric field is at or above the hyperpolarization threshold HPT, the neural fibers within the electric field will block APs that were fired at other points along the fibers. It should be noted here that the magnitude of the hyperpolarization threshold HPT has been estimated to be about 2 to 8 times the magnitude of the depolarization threshold DPT. The hyperpolarizing electric fields generated by upper and lower electrodes $E_U$ and $E_L$ in the exemplary stimulation regimen are below the hyperpolarization threshold HPT at the first fiber bundle FB1. As such, APs in the fiber bundle FB1 that fired at points in the neural fibers adjacent to center electrode $E_C$ will not be blocked at points adjacent the upper and lower electrodes $E_U$, $E_L$. The hyperpolarizing electric fields generated by the upper and lower electrodes $E_U$, $E_L$ will, of course, be even weaker at the second fiber bundle FB2.

In the conventional stimulation regimen described above, the generation of APs in the fibers within the second fiber bundle FB2 will require an increase in the depolarizing electric field generated by the center electrode $E_C$ over that illustrated in FIG. 18. There may be instances where the generation of APs in the first fiber bundle FB1, which necessarily results from the creation of a depolarizing electric field that is strong enough to meet the depolarization threshold DPT at the second fiber bundle FB2, may lead to undesirable outcomes (e.g. discomfort or undesirable reflexive activity) for the patient.

The system 10 may be used to solve this problem by preventing APs generated in the first fiber bundle FB1 from reaching the brain or end organ. Specifically, as illustrated in FIG. 19, one example of a stimulation regimen in accordance with the present invention involves creating local AP blocks that prevent APs created within a portion of the depolarizing electric field that is at or above the depolarization threshold DPT from traveling in both directions beyond the stimulation site. The effective locus of stimulation is, therefore, the region of neural fibers that are generating APs that are not blocked at other portions of the stimulation site.

Here, in the same manner described above with respect to FIG. 18, the upper and lower electrodes $E_U$, $E_L$ are activated as anodes and the center electrode $E_C$ is activated as a cathode. However, the amount of current sunk at the center electrode $E_C$ is sufficient to create a depolarizing electric field that is strong enough to meet the depolarization threshold DPT at the second fiber bundle FB2 and cause fibers within the second fiber bundle to generate APs. Such a depolarizing electric field will, of course, also cause the fibers in the first fiber bundle FB1 to generate APs.

However, at least a substantial portion of the APs in the first fiber bundle FB1 will be prevented from passing electrode $E_U$ by the hyperpolarization. In particular, at least a substantial portion of the APs (i.e., >10-20%) are blocked by hyperpolarizing tissue in the first fiber bundle FB1, located on opposite sides of the tissue in the first fiber bundle FB1 that is generating the APs, to at least the hyperpolarization threshold HPT. This may be accomplished by significantly increasing the level of current sourced from the upper and lower electrodes $E_U$, $E_L$, as compared to the level illustrated in FIG. 18 (e.g., about 2.5 mA each), in order to reach the hyperpolarization threshold HPT within the first fiber bundle FB1 at the upper and lower electrodes $E_U$, $E_L$.

Notably, sinking all of the current sourced by the upper and lower electrodes $E_U$ and $E_L$ at the center electrode $E_C$ could result in a depolarizing electric field that would meet or exceed the depolarization threshold DPT in fiber bundles well beyond the second fiber bundle FB2. In this case, however, a portion of the current sourced by the upper and lower electrodes $E_U$ and $E_L$ is sunk into other electrodes 26 of the stimulation lead 12. That is, the cathodic electrical current is temporarily distributed between the center electrode $E_C$ and other electrodes in accordance with, e.g., the temporal segmentation techniques illustrated in FIGS. 5-12. In the case of the technique illustrated in FIG. 5, the cathodic electrical current is temporarily distributed between the center electrode $E_C$ and non-therapeutic electrodes, with 50% of the cathodic electrical current being delivered to the center electrode $E_C$, and the remaining 50% of the cathodic electrical current being delivered to the non-therapeutic electrodes.

As a result, only a portion of the current sourced by the upper and lower electrodes $E_U$, $E_L$ is sunk into the center electrode $E_C$, thereby allowing the intensity of the depolarizing electric field created by the center electrode $E_C$ to be reduced to a level where the depolarization threshold DPT will not be met in fibers beyond the second fiber bundle FB2. Thus, the electrical current sunk at the center electrode $E_C$ provides therapy to the bodily region (i.e., the dermatome) corresponding to the stimulated portion of the spinal cord (in this case, the buttocks), while the electrical current concurrently sunk at the peripheral electrode(s) provides therapy to the peripheral region, and in this case, the lower back region.

Alternatively, rather the blocking AP in both directions, the stimulation regimen may involve locally blocking APs in a single direction generated in the first fiber bundle FB1. Here, only one of upper and lower electrodes $E_U$, $E_L$ is activated as an anode. In this case, 100% of the total current is being sourced at the upper electrode $E_U$ or lower electrode $E_L$, while the current is being sunk at the center electrode $E_C$ and peripheral electrodes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
 a plurality of electrical terminals configured for being respectively coupled to a plurality of electrodes;
 analog output circuitry configured for delivering electrical pulses to the electrical terminals; and
 control circuitry configured for controlling the analog output circuitry to deliver a plurality of first electrical pulses to a first set of the electrical terminals, the first electrical pulses having a first polarity, to deliver at least a second electrical pulse having a second polarity opposite to the first polarity to a second set of the electrical terminals during the deliverance of each of the first electrical pulses, wherein the at least a second electrical pulse is configured for therapeutically stimulating tissue of the patient, and to deliver at least a third electrical pulse having the second polarity to a third set of the electrical terminals during the deliverance of each of the first electrical pulses, wherein the at least a second electrical pulse and the at least a third electrical pulse are temporarily offset from each other.

2. A method of providing therapy to a patient using the neurostimulation system of claim 1, comprising:
 implanting the plurality of electrodes within the patient;
 delivering the plurality of first electrical pulses to the first set of the electrical terminals, the first electrical pulses having a first polarity;
 delivering the at least a second electrical pulse having a second polarity opposite to the first polarity to the second set of the electrical terminals during the deliverance of each of the first electrical pulses, wherein the at least a second electrical pulse therapeutically stimulates tissue of the patient; and
 delivering the at least a third electrical pulse having the second polarity to the third set of the electrical terminals during the deliverance of each of the first electrical pulses.

3. The method of claim 2, wherein the at least a second electrical pulse comprises a plurality of electrical pulses.

4. The method of claim 2, wherein the at least a third electrical pulse therapeutically stimulates tissue of the patient.

5. The method of claim 2, wherein the at least a third electrical pulse does not therapeutically stimulate tissue of the patient.

6. The method of claim 2, wherein the at least a second electrical pulse and the at least a third electrical pulse do not temporarily intersect each other.

7. The method of claim 2, wherein the magnitudes of the at least a second electrical pulse and the at least a third electrical pulse are equal.

8. The method of claim 2, wherein the widths of the at least a second electrical pulse and the at least a third electrical pulse are equal.

9. The method of claim 2, wherein each of the first electrical pulses is anodic, and the at least a second electrical pulse and the at least a third electrical pulse are cathodic.

10. The method of claim 2, delivering at least a fourth electrical pulse having the second polarity to a fourth set of the electrodes during the deliverance of each of the first electrical pulses, wherein the second, third, and fourth electrical pulses are temporarily offset from each other.

11. The method of claim 2, wherein the tissue is spinal cord tissue.

12. The method of claim 11, wherein the plurality of electrodes is arranged medio-laterally along the spinal cord tissue.

13. The method of claim 11, wherein the second set of electrodes is adjacent dorsal column neural fibers of the spinal cord tissue, the first set of electrodes is adjacent dorsal root neural fibers of the spinal cord tissue, the at least a second electrical pulse generates action potentials in the dorsal column neural fibers, and the at least a first electrical pulse increases the action potential threshold of the dorsal root neural fibers.

14. The method of claim 11, wherein plurality of electrodes is arranged rostro-caudally along the spinal cord tissue.

15. The method of claim 14, wherein the second set of electrodes is a first distance from a first neural fiber bundle and is a second greater distance from a second neural fiber bundle, the at least a second electrical pulse generates action potentials in the first and second neural fibers bundles, and the first electrical pulses block at least some of the action potentials in the first neural fiber bundle.

16. The neurostimulation system of claim 1, wherein the at least a second electrical pulse comprises a plurality of electrical pulses.

17. The neurostimulation system of claim 1, wherein the at least a third electrical pulse is configured for therapeutically stimulating tissue of the patient.

18. The neurostimulation system of claim 1, wherein the at least a third electrical pulse is not configured for therapeutically stimulating tissue of the patient.

19. The neurostimulation system of claim 1, wherein the at least a second electrical pulse and the at least a third electrical pulse do not temporarily intersect each other.

20. The neurostimulation system of claim 1, wherein the magnitudes of the at least a second electrical pulse and the at least a third electrical pulse are equal.

21. The neurostimulation system of claim 1, wherein the widths of the at least a second electrical pulse and the at least a third electrical pulse are equal.

22. The neurostimulation system of claim 1, wherein each of the first electrical pulses is anodic, and the at least a second electrical pulse and the at least a third electrical pulse are cathodic.

23. The neurostimulation system of claim 1, wherein the control circuitry is configured for controlling the analog output circuitry to deliver at least a fourth electrical pulse having the second polarity to a fourth set of the electrodes during the deliverance of each of the first electrical pulses, wherein the at least a second electrical pulse, the at least a third electrical pulse, and the at least a fourth electrical pulse are temporarily offset from each other.

24. The neurostimulation system of claim 1, further comprising at least one lead that carries the electrodes.

25. The neurostimulation system of claim 1, wherein the entireties of the at least a second electrical pulse and the at least a third electrical pulse during the deliverance of each of the first electrical pulses.

* * * * *